US008585235B2

(12) United States Patent
Rockrohr et al.

(10) Patent No.: US 8,585,235 B2
(45) Date of Patent: Nov. 19, 2013

(54) ACCESS ASSEMBLY WITH LANDING LIGHT

(71) Applicant: Covidien LP, Mansfield, MA (US)

(72) Inventors: Brain Rockrohr, Waterbury, CT (US); Michael Bettuchi, Middletown, CT (US); Russell Heinrich, Madison, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/652,541

(22) Filed: Oct. 16, 2012

(65) Prior Publication Data

US 2013/0107508 A1 May 2, 2013

Related U.S. Application Data

(60) Provisional application No. 61/551,957, filed on Oct. 27, 2011.

(51) Int. Cl.
*F21L 4/00* (2006.01)

(52) U.S. Cl.
USPC ..................................... 362/190; 362/249.01

(58) Field of Classification Search
USPC ........ 362/190, 249.01, 249.02, 382, 572, 579
See application file for complete search history.

(56) References Cited

U.S. PATENT DOCUMENTS

| 5,312,393 A | 5/1994 | Mastel |
| 6,551,346 B2 | 4/2003 | Crossley |
| 7,223,233 B2 | 5/2007 | Branch et al. |
| 2001/0053915 A1 | 12/2001 | Grossman |
| 2006/0161117 A1 | 7/2006 | Young |
| 2006/0224045 A1 | 10/2006 | Whipple et al. |
| 2007/0010716 A1 | 1/2007 | Malandain et al. |
| 2007/0100211 A1 | 5/2007 | Selover et al. |
| 2007/0270653 A1 | 11/2007 | Vayser et al. |
| 2008/0045800 A2 | 2/2008 | Farr |
| 2009/0253967 A1 | 10/2009 | Gill et al. |
| 2012/0203168 A1* | 8/2012 | Fujimoto et al. ........... 604/95.01 |

FOREIGN PATENT DOCUMENTS

| EP | 2116201 A1 | 11/2009 |
| EP | 2233089 A1 | 9/2010 |
| EP | 2243436 A2 | 10/2010 |
| EP | 2335622 A2 | 6/2011 |
| WO | WO2005/048814 A2 | 6/2005 |

OTHER PUBLICATIONS

European Search Report EP12190100 dated Jan. 25, 2013.

* cited by examiner

*Primary Examiner* — Mariceli Santiago
*Assistant Examiner* — Glenn Zimmerman

(57) ABSTRACT

An assembly for accessing a body cavity having an illuminated proximal end. The assembly includes a housing defining a longitudinal axis and having a longitudinal opening therethrough for receiving a surgical object, an illumination source disposed adjacent a proximal end of the housing and a sensor mechanism disposed along the longitudinal opening and operably connected to the illumination source. The sensor mechanism is configured to detect the presence of a surgical object within the longitudinal opening and deactivate the illumination source when a surgical object is present in the longitudinal opening.

13 Claims, 5 Drawing Sheets

ACCESS ASSEMBLY WITH LANDING LIGHT

CROSS REFERENCE TO RELATED APPLICATION

The present application claims the benefit of and priority to U.S. Provisional Application Ser. No. 61/551,957, filed on Oct. 27, 2011, the entire contents of which are incorporated herein by reference.

BACKGROUND

1. Technical Field

The present disclosure relates to trocars and other surgical access assemblies. More particularly, the present disclosure relates to lighting mechanisms for illuminating the proximal opening of an access assembly.

2. Background of Related Art

Access assemblies including a source of light for illuminating a surgical site are known. These light sources are generally incorporated into the cannula and/or the housing of the access assemblies. Light from these light assemblies is directed down the cannula and into the body cavity or is shined directly into the body cavity to illuminate the surgical site. Because most access assemblies include one or more seals extending across the longitudinal passage of the assembly, and because the light is directed into the body cavity, the light for illuminating the surgical site is not visible through the proximal end of the assembly.

The lighting within the operating room during a closed procedure is typically dimmer than the lighting in the operating room during an open procedure because the surgeon is viewing the surgical sight on a monitor. The bright light from the monitor used for viewing the surgical site contrasts greatly with the less then optimum lighting in operating room. Thus, locating the opening in an access assembly and directing an instrument through the opening may unnecessary complicate a closed procedure.

Therefore it would be beneficial to have an access assembly that includes a light source for illuminating the proximal end of the access assembly to assist a surgeon in locating the opening within the access assembly and for directing an instrument therethrough.

SUMMARY

Accordingly, an assembly for accessing a body cavity is disclosed. The assembly includes a housing defining a longitudinal axis and having a longitudinal opening therethrough for receiving a surgical object, an illumination source disposed adjacent a proximal end of the housing and a sensor mechanism disposed along the longitudinal opening and operably connected to the illumination source. The sensor mechanism is configured to detect the presence of an instrument within the longitudinal opening and deactivate the illumination source when the instrument is present.

In one embodiment, the assembly further includes a power source operably connected to the sensor mechanism and the illumination source. The sensor mechanism may include at least one transmitter and at least one receiver. The at least one transmitter may be configured to transmit a signal to the receiver. The at least one receiver may be configured to receive a signal from the transmitter. It is envisioned that the signal may be one of radio, magnetic, ultraviolet, infrared or laser. The illumination source may include a plurality of light emitting members extending about the proximal end of the housing. In an alternative embodiment, the illumination source may include a cylindrical tube extending about the proximal end of the housing. In another embodiment, the light emitting members may include light emitting diodes. The illumination source may be configured to illuminate a proximal end of the longitudinal opening.

In one embodiment, the sensor mechanism includes at least a first lever extending into the longitudinal opening in the housing configured to engage an instrument inserted within the longitudinal opening. Deflection of the first lever may operate to deactivate the illumination source. In an alternative embodiment, the sensor mechanism includes first and second contact elements mounted on opposing sides of a slit in a seal member extending across the housing.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment given below, serve to explain the principles of the disclosure, wherein.

DETAILED DESCRIPTION

Figure 1:
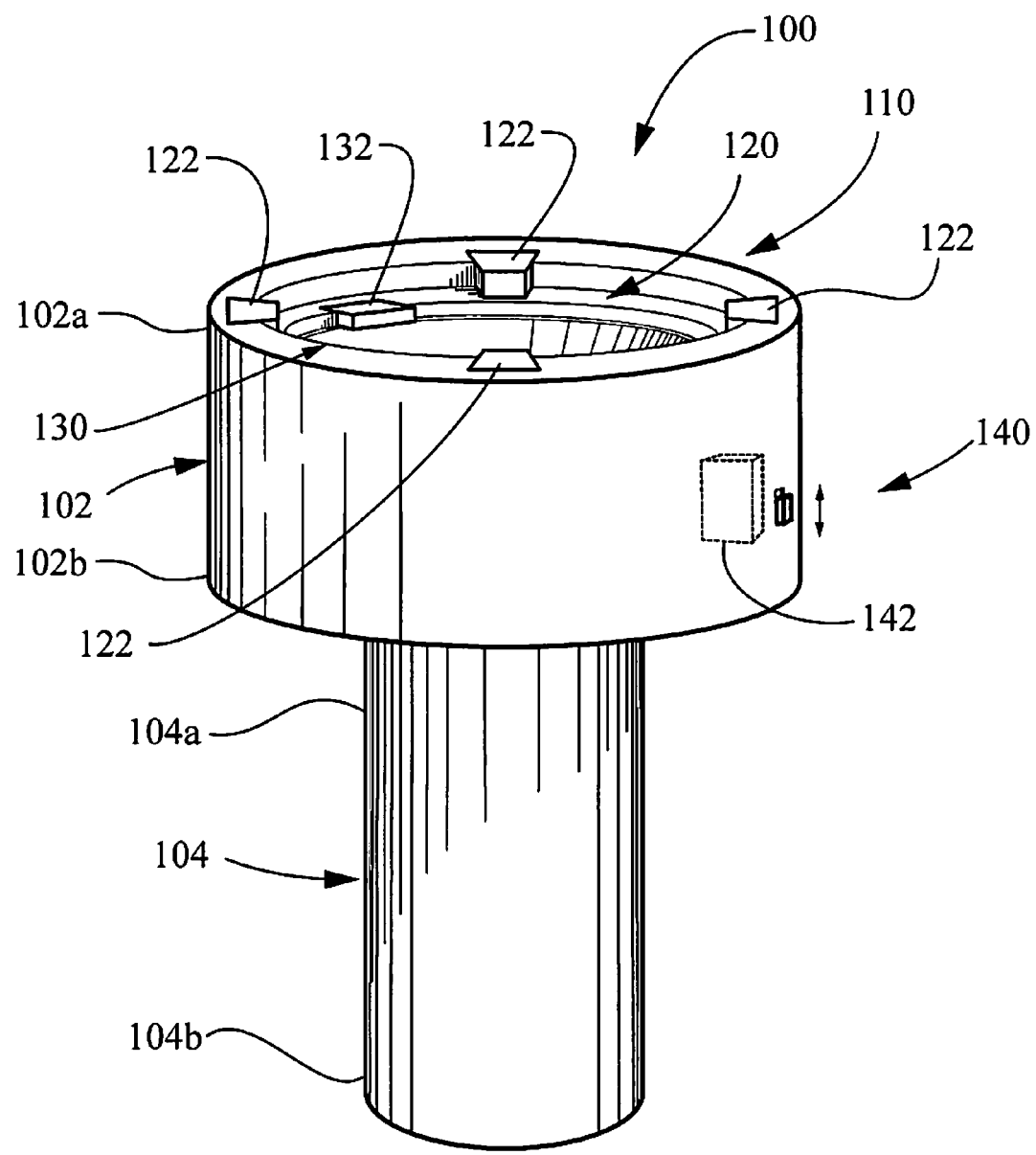
FIG. 1 is a perspective side view of an access assembly according to an embodiment of the present disclosure including an illumination system.
Figure 2:
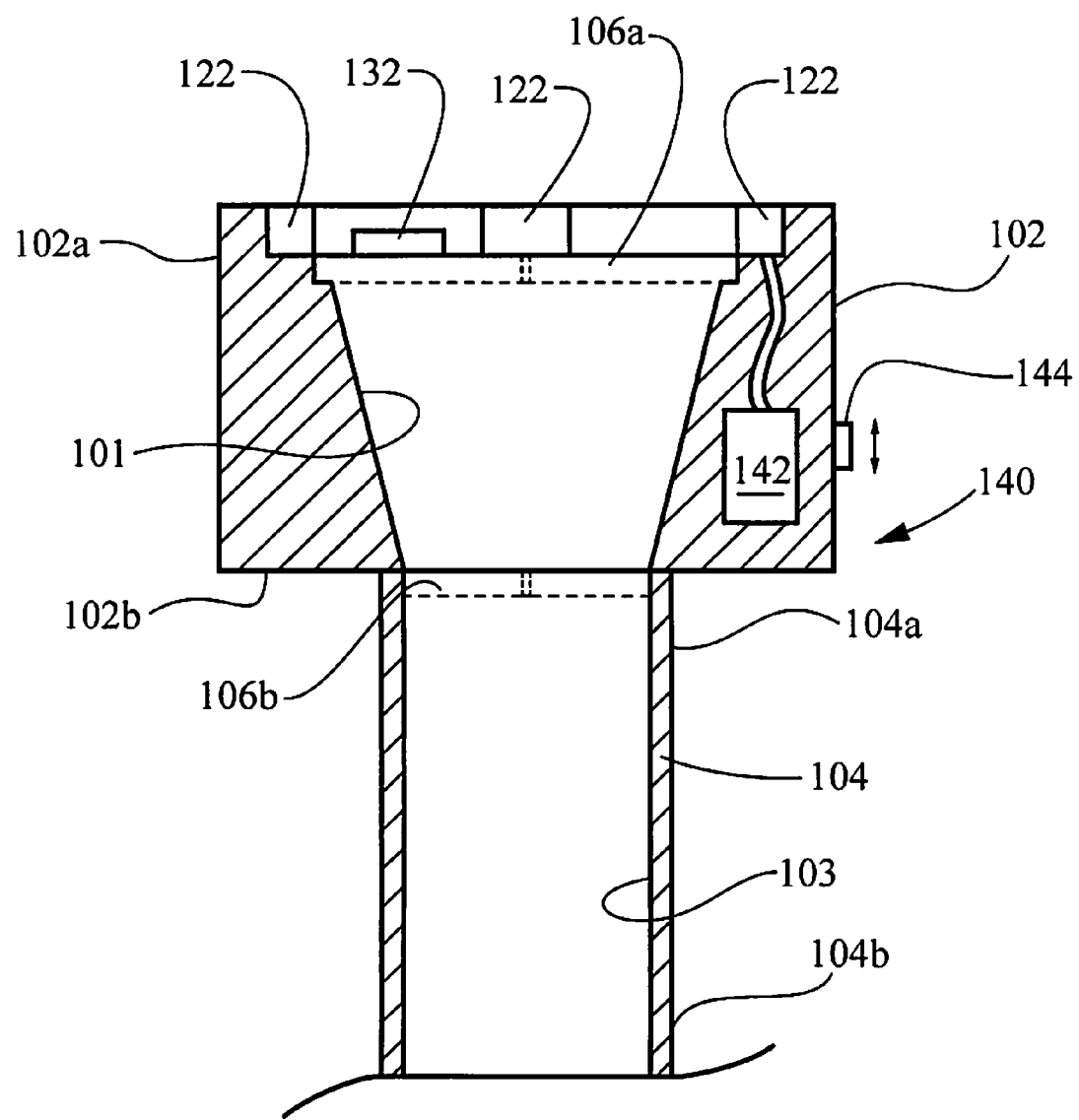
FIG. 2 is a cross-section side view of the access assembly of FIG. 1.

The access assemblies herein disclosed may be configured for use in various surgical procedures, including laparoscopic, endoscopic, arthroscopic and orthopedic surgery. The access assemblies provide passage between the outside atmosphere and a subject's body cavity. The access assemblies are capable of receiving surgical instruments of various sizes and configurations. Embodiments of the presently disclosed access assemblies are configured to receive, for example, clip appliers, graspers, dissectors, retractors, staplers, laser probes, photographic devices, endoscopes and laparoscopes, tubes, and the like. Such instruments are collectively referred to herein as "instruments" or "instrumentation."

Referring now to the drawings wherein like reference numerals illustrate similar components throughout the several views, there are illustrated embodiments of access assemblies according to the principles of the present disclosure. As shown in the drawings and as described throughout the following description, as is traditional when referring to relative positioning on an object, the term "proximal" refers to the end of the apparatus which is closer to the user and the term "distal" refers to the end of the apparatus which is further from the user.

Referring initially to FIGS. 1-4, an embodiment of an access assembly according to the present disclosure is shown generally as access assembly 100. Access assembly 100 includes a housing 102, a sleeve or cannula 104 extending distally from housing 102 and an illumination system 110 configured to illuminate at least a proximal end 102a of housing 102. As will be discussed in further detail below, illumination system 110 includes a light source 120, a sensor mechanism 130 and, optionally, includes a power source 140.

With reference still to FIGS. 1-4, housing 102 defines a substantially cylindrical member having open proximal end 102a, a substantially open distal end 102b, and defining a passageway 101 (FIG. 2) therebetween. Distal end 102b of housing 102 may be integrally formed with sleeve 104. Alternatively, housing 102 may be configured for selectable engagement with sleeve 104. Housing 102 may be constructed of plastic, polymer or other like material. Housing 102 may be disposable, or in the alternative, reusable. Housing 102 may be rigid, or alternatively, substantially flexible. Housing 102 may include one or more seal members 106a having any seal arrangement suitable for receiving an instrument in a sealed manner. As will be discussed in further detail below, proximal end 102a of housing 102 includes lighting system 110.

Still referring to FIGS. 1-4, sleeve 104 is configured to be inserted through the skin of a patient and into a body cavity with the aid of an obturator (not shown), or may instead, include a blade or piercing tip for penetrating through the skin and into a body cavity. Sleeve 104 forms a substantially tubular member having proximal and distal ends 104a, 104b and defining a first longitudinal passage 103 (FIG. 2) extending therebetween. Sleeve 104 may be composed of plastic, metal, polymers or the like. Sleeve 104 may be disposable, or in the alternative, reusable. Sleeve 104 may be rigid, or alternatively, sleeve 104 may be flexible. Sleeve 104 may be open, or instead, may be configured to include one or more seal members 106b disposed along the length thereof. In an alternate embodiment, proximal end 104a of sleeve 104 may be configured for operable engagement with illumination system 110.

With continued reference to FIGS. 1-4, illumination system 110 includes a light source 120, a sensor mechanism 130 and power source 140. Illumination system 110 is configured to illuminate open proximal end 102a of housing 102, and more particularly, the proximal opening to passageway 101, prior to insertion of an instrument "I" (FIG. 4) therethrough. As such, illumination system 110 facilitates insertion of instrument "I" into housing 102.

With reference still to FIGS. 1-4, as shown, illumination source 120 includes a plurality of light emitting members 122 positioned around proximal end 102a of housing 102. Light emitting members 122 may include light emitting diodes ("LEDS"), incandescent, neon or halogen bulbs or lamps, or any other suitable source of light. In one embodiment, LEDS are utilized because of their low wattage power requirement. Alternatively, illumination source 120 may include one or more cylindrical-shaped tubes (FIGS. 7 and 8) extending about passageway 101 in proximal end 102a of housing 102. Light emitting members 122 include light sources of differing colors and/or varying intensities.

Still referring to FIGS. 1-4, sensor mechanism 130 is positioned within passageway 101 of housing 102. Sensor mechanism 130 is configured to detect the presence of instrument "I" within passageway 101. Sensor mechanism 130 is further configured to turn-off or reduce power to illumination source 120 when sensor mechanism 130 detects instrument "I" within passageway 101. In this manner, sensor mechanism 130 is configured to shut-off or dim light source(s) 120. As seen in FIGS. 1-4, sensor mechanism 130 includes a transmitter 132 and a receiver 134. Transmitter 132 is configured to transmit a signal "S", i.e., radio, ultraviolet, infrared, laser, magnetic, etc. Receiver 134 is configured to receive signal "S" transmitted by transmitter 132. In operation, as long as receiver 134 receives a full strength signal from transmitter 132, sensor mechanism 130 completes the circuit between illumination source 120 and power source 140, thereby causing the illumination of light emitting members 122. Receipt of instrument "I" within passageway 101 of housing 102 and between transmitter 132 and receiver 134 interrupts or weakens signal "S" received by receiver 134. The weakened or lack of signal "S" sensed/detected by receiver 134 causes sensor mechanism 130 to disconnect or reduce power to illumination source 120 from power source 140, thereby causing lights 122 to shut off or become dimmer.

In an alternative embodiment, sensor mechanism 130 may have a plurality of transmitters 132 and/or a plurality of receivers 134 disposed within housing 102 about longitudinal passageway 101. Each of the plurality of transmitters 132 may be configured to transmit one or more signals "S" and each of the signals "S" may be the same or different. Similarly, each of the plurality of receivers 134 may be configured to receive one or more signals "S" and each of the signals "S" sensed by the one or more receivers 134 may be the same or different.

Figure 4:
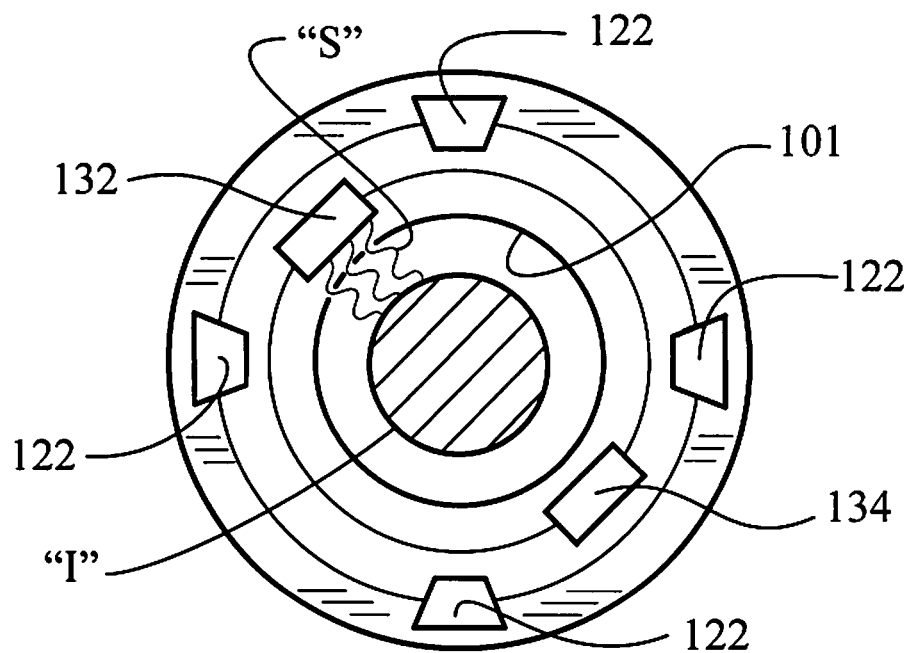
FIG. 4 is a top view of the access assembly of FIGS. 1-3, including an instrument received therethrough.

With continued reference to FIGS. 1 and 4, power source 140 is maintained within housing 102. As shown, power source 140 includes a battery 142. Battery 142 may include any commercially available battery. In one embodiment, battery 142 is rechargeable. Battery 142 may also be replaceable. In an alternative embodiment, illumination system 110 may be configured for operable connection with an external power supply (not shown). In this manner, housing 102 includes an electrical port (not shown) for operably connecting with the external power supply. As shown, power source 140 includes an on/off mechanism 144 in the form of a lever. Alternatively, mechanism 144 may include a bubble button switch, a slide switch, a wheel switch or any other suitable mechanism for activating illumination system 110, including illumination source 120 and sensor mechanism 130.

Figure 3:
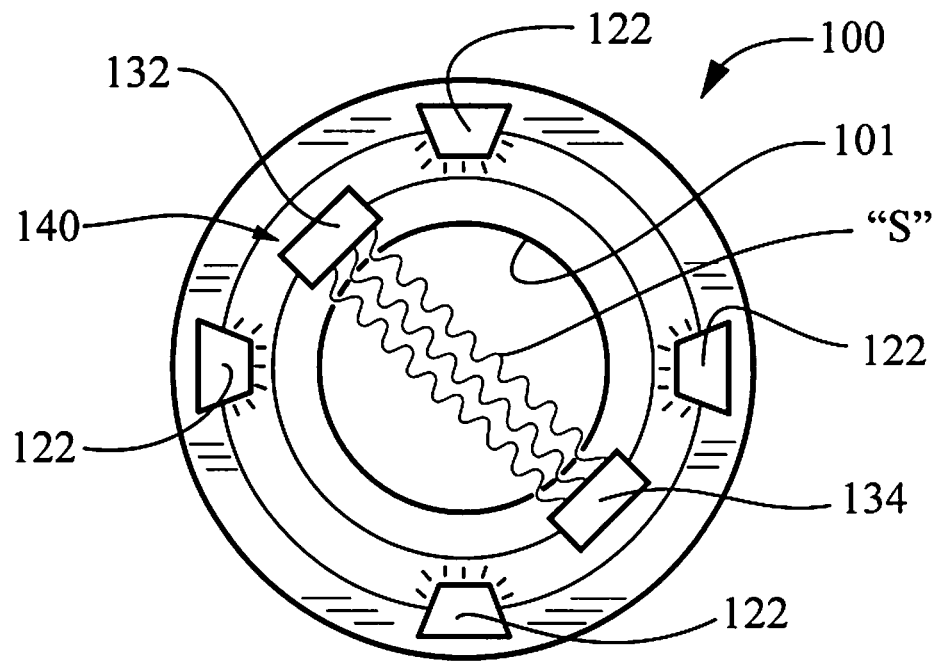
FIG. 3 is a top view of the access assembly of FIGS. 1 and 2, wherein illumination sources of the illumination system are activated.

With particular reference now to FIGS. 3 and 4, access assembly 100 operates in a manner similar to conventional access assemblies. Distal end 104b of sleeve 104 is inserted into a body cavity through tissue, either with a piercing tip (not shown) or with the aid of an obturator (not shown). Once received through the tissue, illumination system 110 is activated by moving switch mechanism 144 of power source 140 to an "on" position. As discussed above, switch mechanism 144 activates illumination source 120 and sensor mechanism 130.

Activating power source 140 causes illumination of light emitting members 122. Light emitting members 122 provide illumination of proximal end 102a of housing 102, thereby facilitating insertion of an instrument "I" within longitudinal opening 101 of housing 102. Reception of instrument "I" within longitudinal opening 101 and between transmitter 132 and receiver 134 of sensor mechanism 130 interrupts or weakens signal "S" emitted by transmitter 132 and detected by receiver 134. The interrupted or weakened signal "S" is detected by receiver 134, thereby causing sensor mechanism 130 to cut-off or reduce power to light emitting member 122. While instrument "I" is maintained within longitudinal opening 101, sensor mechanism 130 maintains illumination source 120 in an off or dimmed condition. Removal of instrument "I" from within passageway 101 returns or strengthens signal "S" detected by receiver 134 of sensor mechanism 130. The return or strengthening of signal "S" detected by receiver 134 causes sensor mechanism 130 to reconnect or increase power to illumination source 120, thereby reilluminating or brightening light emitting members 122.

Figure 5:
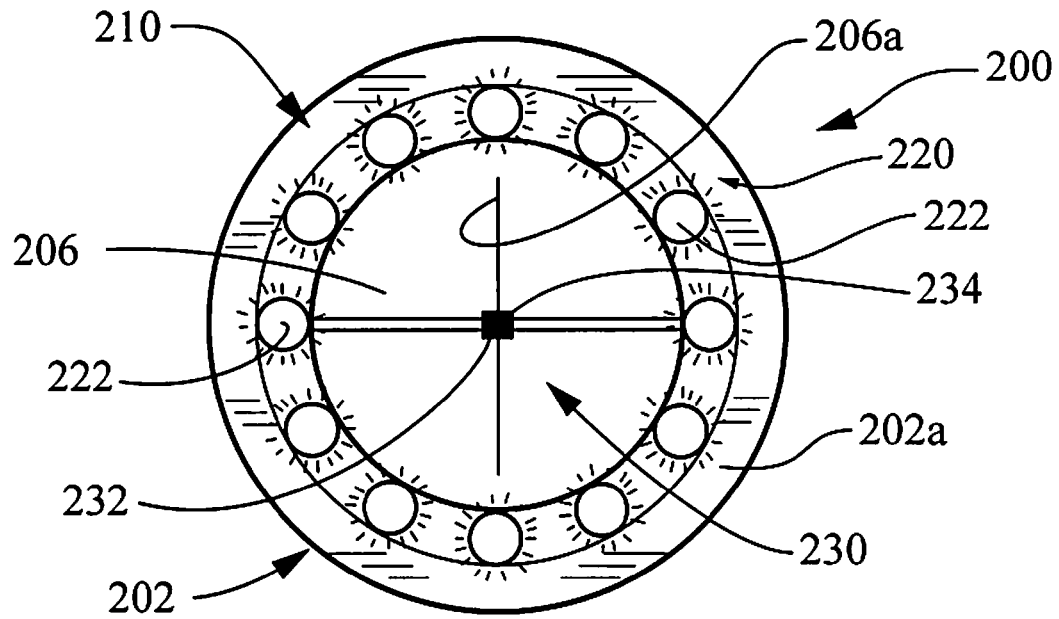
FIG. 5 is a top view of an access assembly according to an alternative embodiment of the present disclosure, wherein the illumination sources of the illumination system are activated.
Figure 6:
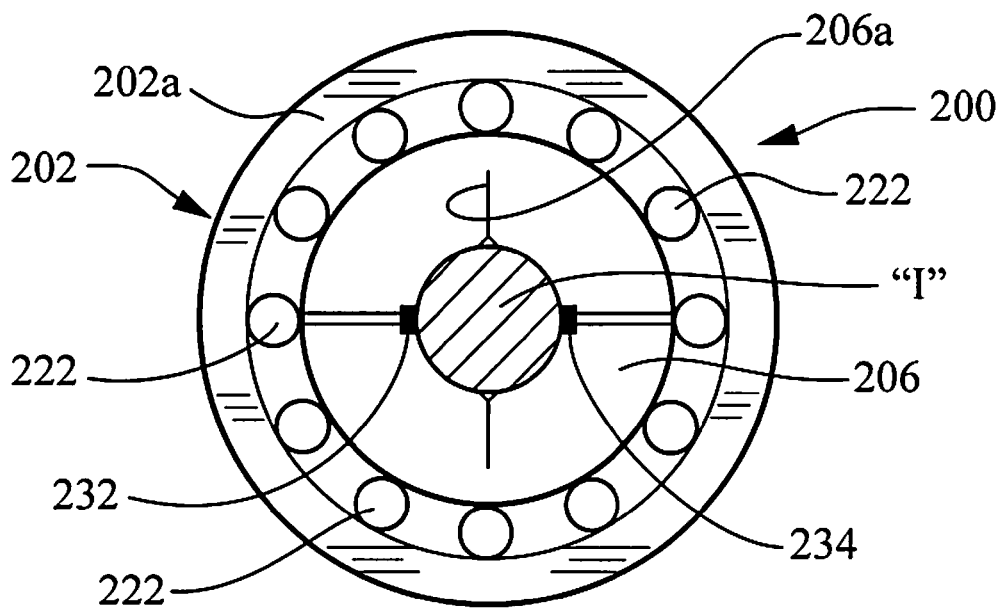
FIG. 6 is a top view of the access assembly of FIG. 5, including an instrument received therethrough.

With reference now to FIGS. 5 and 6, another embodiment of an access assembly according to the present disclosure is shown generally as access assembly 200. Access assembly 200 is substantially similar to access assembly 100, and therefore, will only be described as relates to the differences therebetween. Access assembly 200 includes a housing 202 having a substantially open proximal end 202a. An illumination system 210 is operably received within or about proximal end 202a of housing 202. A seal member 206 extends across housing 202 and is configured to receive instrument "I" therethrough in a sealed manner.

With reference still to FIGS. 5 and 6, illumination system 210 includes an illumination source 220 and a sensor mechanism 230. Illumination source 210 includes a plurality of light emitting sources 222. Light emitting sources 222 extend about proximal end 202a of housing 202 and are configured to illuminate proximal end 202a of housing 202. Sensor mechanism 230 includes first and second contact elements 232, 234. Contact elements 232, 234 are received on opposite sides of a slit 206a formed in seal member 206. When seal member 206 is in a closed configuration (FIG. 5), contact elements 232, 234 are disposed adjacent one another and may be in contact with one another. In the closed configuration, the close proximity of first contact element 232 with second contact element 234 completes a circuit within sensor mechanism 230 which permits illumination of light emitting sources 222. Receipt of instrument "I" through slit 206a in seal member 206 causes the separation of first and second contact members 232, 234. The separation of contact members 232, 234 breaks the circuit within sensor mechanism 230, thereby disconnecting power to light emitting sources 222. Removal of instrument "I" from within slit 206a of seal member 206 permits first and second contact members 232, 234 to return to the initial, approximated position, thereby reconnecting the circuit within sensor mechanism 230 and returning power to illumination source 220.

Figure 7:
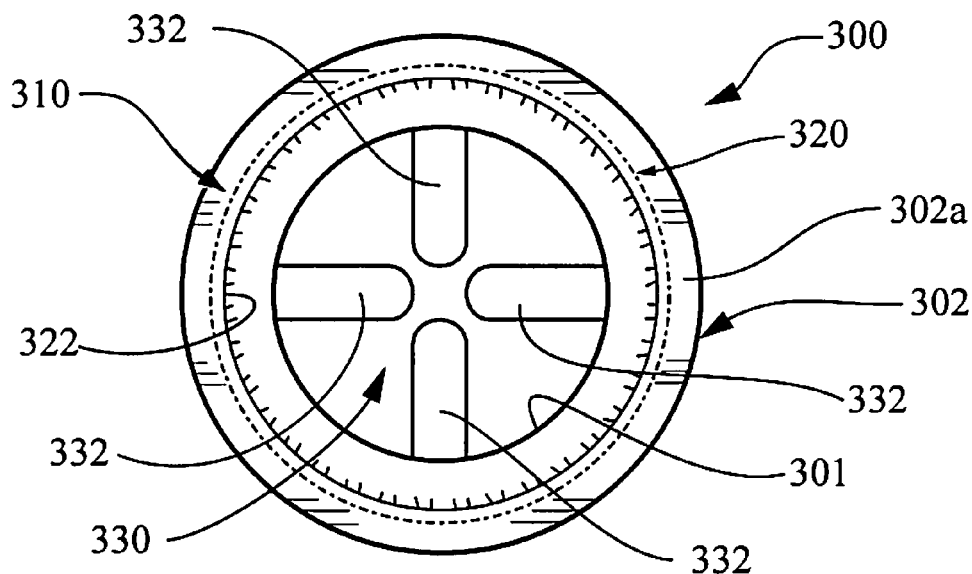
FIG. 7 is a top view of an access assembly according to another embodiment of the present disclosure, wherein the illumination source of the illumination system is activated.
Figure 8:
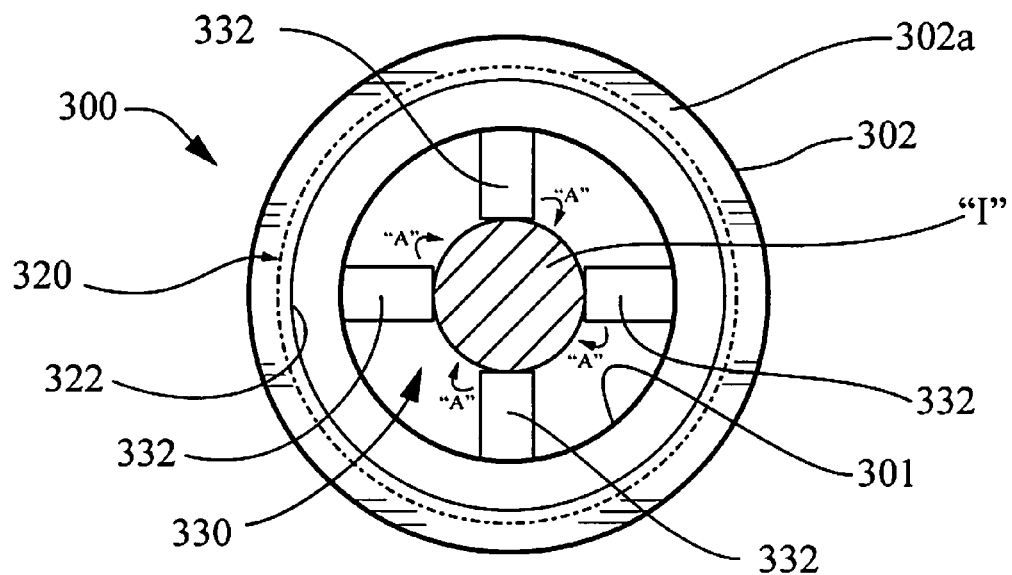
FIG. 8 is a top view of the access assembly of FIG. 7, including an instrument received therethrough.

Referring now to FIGS. 7 and 8, still another embodiment of an access assembly according to the present disclosure is shown generally as access assembly 300. Access assembly 300 includes an illumination system 310. Illumination system 310 includes an illumination source 320 in the form of a cylindrical-shaped tube 322. Tube 322 is disposed within a proximal end 302a of housing 302 and about a proximal opening of passageway 301. Tube 322 is configured to illuminate proximal end 302a of housing 302. Access assembly 300 further includes a sensor mechanism 330. Sensor mechanism 330 includes a plurality of levers 332 extending within passageway 301 of housing 302. Each of levers 332 is pivotally connected to housing 302. Levers 332 are configured to pivot downward, as indicated by arrows "A" (FIG. 8), upon engagement within an instrument "I" to break or interrupt a circuit (not shown) within sensor mechanism 330.

With continued reference to FIGS. 7 and 8, in an initial configuration (FIG. 7) and prior to insertion of instrument "I" within passageway 301 of housing 302, levers 332 are biased across passageway 301. Sensor mechanism 330 is configured such that when levers 332 are biased to the initial position, the circuit (not shown) within sensor mechanism 330 is connected, thereby providing power to illumination source 320 and causing the illumination of light 322. Turning to FIG. 8, receipt of instrument "I" within passageway 301 causes downward deflection of at least one lever 332. Defection of one or more levers 332 disconnects the circuit within sensor mechanism 330, thereby cutting the power to illumination source 320 and causing light 322 to shut off or dim. Retraction of instrument "I" from within passageway 301 permits the return of levers 332 to an initial, non-deflected condition, thereby completing the circuit within sensor mechanism 320 and returning power to illumination source 320.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, the housing may include a glow-in-the-dark material on a proximal end thereof for illuminating the proximal end of the housing without the need for a power source. In another embodiment, the light sources may be configured to blink or otherwise change intensities or colors in response to the presence of an instrument within the housing.

The invention claimed is:

1. An assembly for accessing a body cavity, the assembly comprising:
    a housing defining a longitudinal axis and having a longitudinal opening therethrough for receiving a surgical object;
    an illumination source disposed adjacent a proximal end of the housing; and
    a sensor mechanism disposed along the longitudinal opening and operably connected to the illumination source, wherein the sensor mechanism is configured to detect the presence of a surgical object within the longitudinal opening and deactivate the illumination source when the surgical object is present in the longitudinal opening.

2. The assembly according to claim 1, further including a power source operably connected to the sensor mechanism and the illumination source.

3. The assembly according to claim 1, wherein the sensor mechanism includes at least one transmitter and at least one receiver.

4. The assembly according to claim 3, wherein the at least one transmitter is configured to transmit a signal to the receiver.

5. The assembly according to claim 3, wherein the at least one receiver is configured to receive a signal from the transmitter.

6. The assembly according to claim 4, wherein the signal is one of radio, magnetic, ultraviolet, infrared or laser.

7. The assembly according to claim 1, wherein the illumination source includes a plurality of light emitting members extending about the proximal end of the housing.

8. The assembly according to claim 1, wherein the illumination source includes a cylindrical tube extending about the proximal end of the housing.

9. The assembly according to claim 1, wherein the illumination source is configured to illuminate a proximal end of the longitudinal opening.

10. The assembly according to claim 1, wherein the sensor mechanism includes at least a first lever extending into the longitudinal opening in the housing configured to engage a surgical object inserted within the longitudinal opening.

11. The assembly according to claim 10, wherein deflection of the first lever deactivates the illumination source.

12. The assembly according to claim 1, wherein the sensor mechanism includes first and second contact elements mounted on opposing sides of a slit in a seal member extending across the housing.

13. The assembly according to claim 7, wherein the light emitting members are light emitting diodes.

* * * * *